United States Patent
Lee et al.

(10) Patent No.: US 9,879,060 B2
(45) Date of Patent: Jan. 30, 2018

(54) SV82 POLYPEPTIDE, AND COSMETIC COMPOSITION FOR REDUCING SKIN WRINKLES AND MAINTAINING SKIN ELASTICITY COMPRISING SV82 POLYPEPTIDE AS ACTIVE INGREDIENT

(71) Applicant: NEXGEN BIOTECHNOLOGIES, INC., Seoul (KR)

(72) Inventors: Sun Kyo Lee, Gyeonggi-do (KR); Je Geun Yoo, Daejeon (KR); Seong Ran Lee, Gyeonggi-do (KR); Han Bong Ryu, Seoul (KR); Tae Won Choi, Seoul (KR); Jong Nam Choi, Gyeonggi-do (KR); Tae Hyun Kim, Incheon (KR)

(73) Assignee: NEXGEN BIOTECHNOLOGIES, INC., Seoul (KR)

( * ) Notice: Subject to any disclaimer, the term of this patent is extended or adjusted under 35 U.S.C. 154(b) by 0 days.

(21) Appl. No.: 15/248,092

(22) Filed: Aug. 26, 2016

(65) Prior Publication Data

US 2017/0190747 A1 Jul. 6, 2017

(30) Foreign Application Priority Data

Dec. 30, 2015 (KR) .................. 10-2015-0189555

(51) Int. Cl.
| | | |
|---|---|---|
| *A61K 38/00* | (2006.01) | |
| *C07K 14/435* | (2006.01) | |
| *A61K 8/64* | (2006.01) | |
| *A61Q 19/08* | (2006.01) | |
| *A61K 8/02* | (2006.01) | |

(52) U.S. Cl.
CPC ...... *C07K 14/43518* (2013.01); *A61K 8/0216* (2013.01); *A61K 8/64* (2013.01); *A61Q 19/08* (2013.01)

(58) Field of Classification Search
None
See application file for complete search history.

(56) References Cited

FOREIGN PATENT DOCUMENTS

| | | |
|---|---|---|
| CN | 101585872 A | 11/2009 |
| EP | 0374940 B1 | 12/1993 |
| EP | 2705830 A1 | 3/2014 |
| KR | 10-2013-0102698 A | 9/2013 |
| WO | 2007065925 A2 | 6/2007 |
| WO | 2008061329 A2 | 5/2008 |
| WO | 2013156064 A1 | 10/2013 |
| WO | WO 2013/156064 * | 10/2013 |

OTHER PUBLICATIONS

Vassilevski et al. (J Biol Chem. Oct. 15, 2010;285(42):32293-302).*
Meng et al. (PLoS One. 2011;6(6):e21608).*
F.S. Torres et al., Toxicon, vol. 56, No. 7, 2010, p. 1172-1180.
European Search Report for EP16195913.5 from European patent office in a counterpart European patent application.
Hanahan, D. Studies on transformation of *Escherichia coli* with plasmids. J.Mol.Biol. 1983. 166:557-580.

* cited by examiner

*Primary Examiner* — Jennifer Pitrak McDonald
*Assistant Examiner* — Sergio Coffa
(74) *Attorney, Agent, or Firm* — The PL Law Group, PLLC (57) ABSTRACT

A spider venom (SV) 82 polypeptide has an amino acid sequence of SEQ ID NO: 2. An SV82 polypeptide-encoding gene having a nucleotide sequence of SEQ ID NO: 1 which is optimized for *E. coli* codon. A recombinant vector includes the SV82 polypeptide-encoding gene, An *E. coli* is transformed with the recombinant vector. A method of producing SV82 polypeptide includes transforming a host cell with the recombinant vector. A cosmetic composition for reducing skin wrinkles and maintaining skin elasticity includes SV82 polypeptide as an active ingredient.

13 Claims, 5 Drawing Sheets

FIG. 1

Schematic diagram to explain how SV82-expressing plasmid is manufactured

SEQUENCE LISTING

<160> NUMBER OF SEQ ID NOS: 4

<210> SEQ ID NO 1
<211> LENGTH: 240
<212> TYPE: DNA
<213> ORGANISM: Artificial Sequence
<220> FEATURE:
<223> OTHER INFORMATION: SV82

<400> SEQUENCE: 1
atgaaatacc tgctgccgac cgctgctgct ggtctgctgc tcctcgctgc ccagccggcg     60
atggccaggg ctacctgtgc agggcaggat cagccatgca agaaacgtg cgattgctgt      120 ggcgaacgtg gcgaatgcgt gtgtggtggt ccgtgcattt gtcgccaagg ctatttctgg    180
attgcgtggt acaaactggc gaactgcaag aaactcgagc accaccacca ccaccactga   240

<210> SEQ ID NO 2
<211> LENGTH: 79
<212> TYPE: PRT
<213> ORGANISM: Artificial Sequence
<220> FEATURE:
<223> OTHER INFORMATION: SV82

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Arg Ala Thr Cys Ala Gly Gln Asp Gln Pro
            20                  25                  30

Cys Lys Glu Thr Cys Asp Cys Cys Gly Glu Arg Gly Glu Cys Val Cys
        35                  40                  45

Gly Gly Pro Cys Ile Cys Arg Gln Gly Tyr Phe Trp Ile Ala Trp Tyr
    50                  55                  60

Lys Leu Ala Asn Cys Lys Lys Leu Glu His His His His His His
65                  70                  75

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cagccatgca aagaaacgtg                                                  20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtgctcgag tttcttgcag                                                  20

SV82 POLYPEPTIDE, AND COSMETIC COMPOSITION FOR REDUCING SKIN WRINKLES AND MAINTAINING SKIN ELASTICITY COMPRISING SV82 POLYPEPTIDE AS ACTIVE INGREDIENT

CROSS-REFERENCE TO RELATED APPLICATION

This application claims the benefit of Korean Patent Application No. 10-2015-0189555, filed on Dec. 30, 2015, in the Korean Intellectual Property Office, the disclosure of which is incorporated herein in its entirety by reference.

BACKGROUND

1. Technical Field

The present disclosure relates to spider venom (SV) 82 polypeptide and a cosmetic composition for reducing skin wrinkles and maintaining skin elasticity comprising SV82 polypeptide as active ingredient.

2. Description of the Related Art

In the spider venom of *Phoneutria nigriventer*, PnTx2-6 consists of many glutamates and many signal peptides, in other words, 403 nucleotides. It is known that PnTx2-6 affects a sodium ion channel flow and induces erection of a mouse under anesthesia.

As a spider venom of *Phoneutria nigriventer*, 100 or more polypeptides having the size of 3,500 to 9,000 Da are known, and in a tetrodotoxin (TTX)-sensitive way, secretion of acetylcholine and glutamate is induced, thereby causing a greater flow of sodium ions into cortical synaptosomes and the prevention of inactivation of the sodium channel. Accordingly, priapism occurs.

PnTx2-6, included in the spider venom of *Phoneutria nigriventer* inducing priapism, is a natural protein that is an alternative to Viagra, and research thereinto has been globally continued after 2010. However, up until now, the intramolecular mechanism on how PnTx2-6 acts has not been known. Also, no research results for production of PnTx2-6 in great quantities for use as a natural protein alternative to Viagra have been disclosed.

PnTx2-6 of *Phoneutria nigriventer* is a polypeptide that has the molecular weight of about 9 kDa and consists of 82 amino acids and 10 cysteines. After PnTx2-6 polypeptide is known as a material inducing priapism through a sodium ion channel, the inventors of the present application have made efforts to use SV82 polypeptide as in aesthetic plastic surgery and cosmetic compositions, to which the SV82 polypeptide has not been applied. However, how natural PnTx2-6 polypeptide is extracted from *Phoneutria nigriventer* is not known, and also, how SV82 polypeptide is extracted is not known. Accordingly, genetic engineering is necessarily required to produce SV82 polypeptide. In PnTx2-6 polypeptide, as described above, 10 cysteines form cysteine knots together. Accordingly, a chemical synthesis method, an extracellular isolation method using a yeast, and a method using a fusion partner protein to obtain a peptide with its intrinsic three-dimensional structure are not appropriate for producing PnTx2-6 polypeptide in great quantities. Accordingly, to prevent endotoxin which needs to be taken into consideration in intramolecular production using *E. coli*, the inventors of the present application used inclusion bodies to produce SV82 polypeptide in great quantities.

European Patent No. 0374940 discloses 'Polypeptides isolated from the venom of the spider hololena curta', and Korean Patent Publication No. 2013-0102698 discloses 'a *Vespa mandarina* hornet venom extraction method, and a functional cosmetic composition using the same.' However, these disclosures fail to disclose SV82 polypeptide and a cosmetic composition for reducing skin wrinkles and maintaining skin elasticity comprising SV82 polypeptide as an active ingredient.

SUMMARY

The inventors of the present application optimized spider venom (SV) 82 gene derived from PnTx2-6 gene with respect to a codon of *Escherichia coli* (*E. coli*), produced a recombinant vector by using the optimized SV gene, and transformed *E. coli* with the recombinant vector to produce SV82 polypeptide. Also, the inventors of the present application used SV82 polypeptide as an active ingredient in various formulations for cosmetic products (skin, essence, lotion, and cream), and performed a skin test on test participants by using the produced formulations to identify skin wrinkles reducing effects and skin elasticity maintaining effects, thereby completing the present disclosure.

Additional aspects will be set forth in part in the description which follows and, in part, will be apparent from the description, or may be learned by practice of the presented embodiments.

The present disclosure provides a SV82 polypeptide having the amino acid sequence of SEQ ID NO: 2.

The present disclosure also provides a SV82 polypeptide-encoding gene having the nucleotide sequence of SEQ ID NO: 1, the gene optimized for a codon of *E. coli*.

The present disclosure also provides a recombinant vector comprising the SV82 polypeptide-encoding gene.

The present disclosure also provides *E. coli* transformed with the recombinant vector.

The present disclosure also provides a method of producing SV82 polypeptide in a host cell, the method comprising transforming the host cell with the recombinant vector.

The present disclosure also provides a cosmetic composition for reducing skin wrinkles and maintaining skin elasticity comprising SV82 polypeptide having the amino acid sequence of SEQ ID NO: 2 as an active ingredient.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

The present disclosure provides a spider venom (SV) 82 polypeptide having the amino acid sequence of SEQ ID NO: 2.

The SV82 polypeptide according to the present disclosure includes a protein having the amino acid sequence of SEQ ID NO: 2 or a functional equivalent to the protein. The term "functional equivalent" used herein refers to a protein that has the sequence identity of at least 70% or more, 80% or more, 90% or more, or 95% or more to the amino acid sequence of SEQ ID NO: 2 due to addition, substitution, or deletion of amino acids, and has substantially homogenous activity as the protein set forth in SEQ ID NO: 2. The term "substantially homogenous activity" used herein refers to an activity for reducing skin wrinkles and maintaining skin elasticity. The present disclosure also provides a fragment, derivative and analogues of the SV82 polypeptide. The terms "fragment", "derivative" and "analogues" as used herein each refer to a polypeptide that has substantially the same biological function or activity as SV82 polypeptide according to the present disclosure.

The present disclosure also provides a SV 82 polypeptide-encoding gene having the nucleotide sequence of SEQ ID NO: 1, wherein the SV82 polypeptide-encoding gene is optimized for *E. coli*.

The SV82 polypeptide-encoding gene according to the present disclosure may have the nucleotide sequence of SEQ ID NO: 1. A homolog of the sequence is included in the scope of the present disclosure. In detail, the gene may include any sequence having the sequence identity of 70% or more, 80% or more, 90% or more, or 95% or more to the nucleotide sequence of SEQ ID NO: 1. The term "sequence identity of . . . %" with respect to a polynucleotide is identified by comparing two optimally arranged sequences with a comparative domain. A part of a polynucleotide sequence in the comparative region may include an addition or deletion (that is, a gap) compared to a reference sequence (that does not include the addition or deletion) with respect to the optimal alignments of two sequences.

The term "optimizing codon" refers to changing a codon of polynucleotide that encodes a protein in such a way that a coded protein is efficiently expressed with priority in an organism. Gene code is degenerative in view that most amino acids are represented by several codons called "synonymous" or "synonym" codon, and codon usage by a particular organism is not arbitrary, but biased to a particular codon triplet. The biased codon usage may more highly likely occur in association with some genes, genes that have a common function and a common ancestor, a low copy-number protein over a highly expressed protein, and a collective protein-coding domain of organism genome. In one embodiment, the nucleotide sequence of SEQ ID NO: 1 has been optimized for a codon of *E. coli* to allow SV82 gene, which is derived from a spider, to be expressed inside *E. coli*.

The present disclosure also provides a recombinant vector comprising the SV82 polypeptide-encoding gene and an *E. coli* that is transformed with the recombinant vector.

The term "recombinant" cell as used herein refers to a cell that replicates a foreign nucleic acid, expresses the nucleic acid, or expresses a protein that has been coded by a peptide, a foreign peptide, or a foreign nucleic acid. The recombinant cell may express a gene or gene fragment that does not naturally exist in the form of a sense or an antisense. In one embodiment, however, the recombinant cell can express a gene that exists in a natural form thereof. In this case, the gene is a modified gene and re-introduced into the cell by using an artificial method.

In one embodiment, the SV82 polypeptide-encoding gene may be inserted into a recombinant expression vector. The term "recombinant expression vector" used herein refers to a bacterial plasmid, a phage, a yeast plasmid, a plant cell virus, a mammal cell virus, or other vectors. The recombinant expression vector may be any plasmid or vector that can be replicated and stabilized in a host. The expression vector may have an origin of replication, a promoter, a marker gene, and a translation control element.

A SV82 polypeptide-encoding gene sequence and an expression vector including an appropriate transcription/translation signal may be constructed by using a method known to one of ordinary skill in the art. The method includes in-vitro recombinant DNA technology, DNA synthesis technology, in-vivo recombinant technology, etc. A DNA sequence may be effectively ligated to an appropriate promoter inside an expression vector to induce synthesis of mRNA. The expression vector may include, as a translation initiation site, a ribosome binding site and a transcription terminator.

In one embodiment, the recombinant vector may be a vector that is synthesized by fusing pET22b vector with a synthesized gene (SEQ ID NO: 1) that encodes SV82 polypeptide in frame at 5' terminus (NcoI restriction enzyme site) and at 3' terminus (XhoI restriction enzyme site), and the gene is effectively expressed by lac promoter and lac I repressor to produce SV82 polypeptide.

A host cell for the vector according to the present disclosure may be any host cell in the art that allows the vector to be stably and continuously cloned and expressed in a prokaryotic cell. For example, the host cell available herein may be *E. coli* Rosetta, *E. coli* JM109, *E. coli* BL21, *E. coli* RR1, *E. coli* LE392, *E. coli* B, *E. coli* X 1776, *E. coli* W3110, *Bacillus* sp. strain, such as *Bacillus subtilis* or *Bacillus thuringiensis*, or intestinal bacteria and strain, such as *Salmonella typhimurium*, *Serratia marcescens*, or various *Pseudomonas* sp.

When the vector according to the present disclosure is used to transform an eukaroytic cell, an available host cell herein may be a yeast (*Saccharomyces cerevisiae*), an insect cell, a human cell (for example, CHO cell line (Chinese hamster ovary), W138, BHK, COS-7, 293, HepG2, 3T3, RIN, and MDCK cell lines), or a plant cell.

An example of the transformed host cell as the recombinant vector may be *E. coli* Rosetta2 (DE3) pLysS *E. coli*, but is not limited thereto.

When the host cell is a procaryotic cell, the vector may be delivered into the host cell by using, for example, a $CaCl_2$ method, a Hanahan method (D., 1983 J. Mol. Biol. 166, 557-580), or an electroporation method. When the host cell is a eukaroytic cell, the vector may be delivered into the host cell by using, for example, microinjection, calcium phosphate precipitation, electroporation, liposome-mediated transfection, DEAE-dextran treatment, or gene bombardment.

The present disclosure also provides a method of producing SV82 polypeptide in a host cell by transforming the host cell with the recombinant vector.

In one embodiment, the host cell may be *E. coli*. In one embodiment, the host cell may be *E. coli* Rosetta2 (DE3) pLysS *E. coli*, but is not limited thereto.

The present disclosure also provides a cosmetic composition for reducing skin wrinkles and maintaining skin elasticity comprising SV82 polypeptide having the amino acid sequence of SEQ ID NO: 2 as an active ingredient.

Due to the inclusion of SV82 polypeptide as an active ingredient in the cosmetic composition, SV82 polypeptide derives cellular priapism by intradermal peripheral nerve stimulation to reduce skin wrinkles and maintain skin elasticity.

In one embodiment, the amount of the SV82 polypeptide in the cosmetic composition may be in a range of 0.000001 to 0.0001 wt % based on the total weight or the cosmetic composition.

When the amount of the SV82 polypeptide is less than 0.000001 wt %, effects for reducing skin wrinkles and maintaining skin elasticity are negligible, and when the amount of the SV82 polypeptide is 0.0001 wt % or more, the formed formulations may have problems in terms of safety and stability.

The cosmetic composition according to the present disclosure includes, in addition to the active ingredient, components that are conventionally used in a cosmetic composition. Examples of such conventional components include a fatty substance, an organic solvent, a solubilizer, a thickening agent, a gelling agent, a softener, an antioxidant, a suspending agent, a stabilizer, a foaming agent, an odorant, a surfactant, water, an ionic or non-ionic emulsifying agent, a filler, an agent for blocking metallic ions, a chelating agent, a preserving agent, a vitamin, a blocker, a moisturizing agent, essential oil, a dye, a pigment, a hydrophilic or hydrophobic activator, a conventional adjuvant, such as lipid vesicle, and a carrier.

The cosmetic composition according to the present disclosure may be prepared in any formulation that is used in the related art. Examples of the formulation available herein include a solution, a suspension, an emulsion, paste, gel, cream, lotion, powder, oil, powder foundation, emulsion foundation, wax foundation, and spray, but are not limited thereto. Examples of these formulations include skin lotion, skin softener, skin toner, astringent, lotion, milk lotion, moisture lotion, nutrition lotion, massage cream, nutrition cream, eye cream, moisture cream, hand cream, essence, nutrition essence, pack, cleansing foam, cleansing water, cleansing lotion, cleansing cream, body lotion, body cleanser, a soap, and a cosmetic powder formulation.

When the cosmetic composition according to the present disclosure is prepared in the formation of paste, cream, or gel, an available carrier herein may be animal oil, plant oil, wax, paraffin, starch, tracanth, a cellulose derivative, polyethylene glycol, silicon, bentonite, silica, talc, zinc oxide, etc.

When the cosmetic composition according to the present disclosure is prepared in the formation of powder or spray, an available carrier herein may be lactos, talc, silica, aluminum hydroxide, calcium silicate, or polyamide powder. When the cosmetic composition is prepared in the powder formation, the cosmetic composition may additionally include a propelling agent, such as chlorofluoro hydrocarbon, propane/butane, or dimethyl ether.

When the cosmetic composition according to the present disclosure is prepared in the formation of a solution or an emulsion, an available carrier herein may be a solvent, a solubilizer, or an emulsifying agent. Examples thereof include water, ethanol, isopropanol, ethyl carbonate, ethyl acetate, benzyl alcohol, benzyl benzoate, propyleneglycol, 1,3-butylglycol oil, glycerol aliphatic ester, polyethylene glycol, and fatty acid ester of sorbitan.

When the cosmetic composition according to the present disclosure is prepared in the formation of a suspension, an available carrier herein may be a liquid diluent, such as water, ethanol, or propyleneglycol; a suspending agent, such as ethoxylated isostearyl alcohol, polyoxyethylene sorbitol ester, or polyoxyethylene sorbitan ester; microcrystalline cellulose, aluminium meta-hydroxide, bentonite, aga, tracanth, etc.

Hereinafter, embodiments of the present disclosure will be described in detail with reference to examples below. However, the examples are provided herein only for illustrative purpose, and do not limit the present disclosure.

Example 1. Preparation of Recombinant Expression Vector for Expressing in *E. coli* to Produce SV82 Polypeptide and Transformed Recombinant Microorganism A gene that encodes SV82 polypeptide and is optimized for *E. coli*, recombinant expression vector, and transformed recombinant microorganism were prepared as follows.

A SV82 polypeptide-encoding gene (SEQ ID NO: 1) fragment that is optimized for expressing SV82 polypeptide in *E. coli* and encodes 79 amino acids was manufactured and synthesized by using a polypeptide-encoding gene as a template. Primers used during the synthesis are as follows:

```
Forward primer: 5'-CAGCCATGCAAAGAAACGTG-3'
(underlined, Nco I restriction enzyme site; SEQ ID
NO: 3);
and Reverse primer: 5'-GGTGCTCGAGTTTCTTGCAG-3'
(underlined, Xho I restriction enzyme site; SEQ
ID NO: 4).
```

Figure 1:
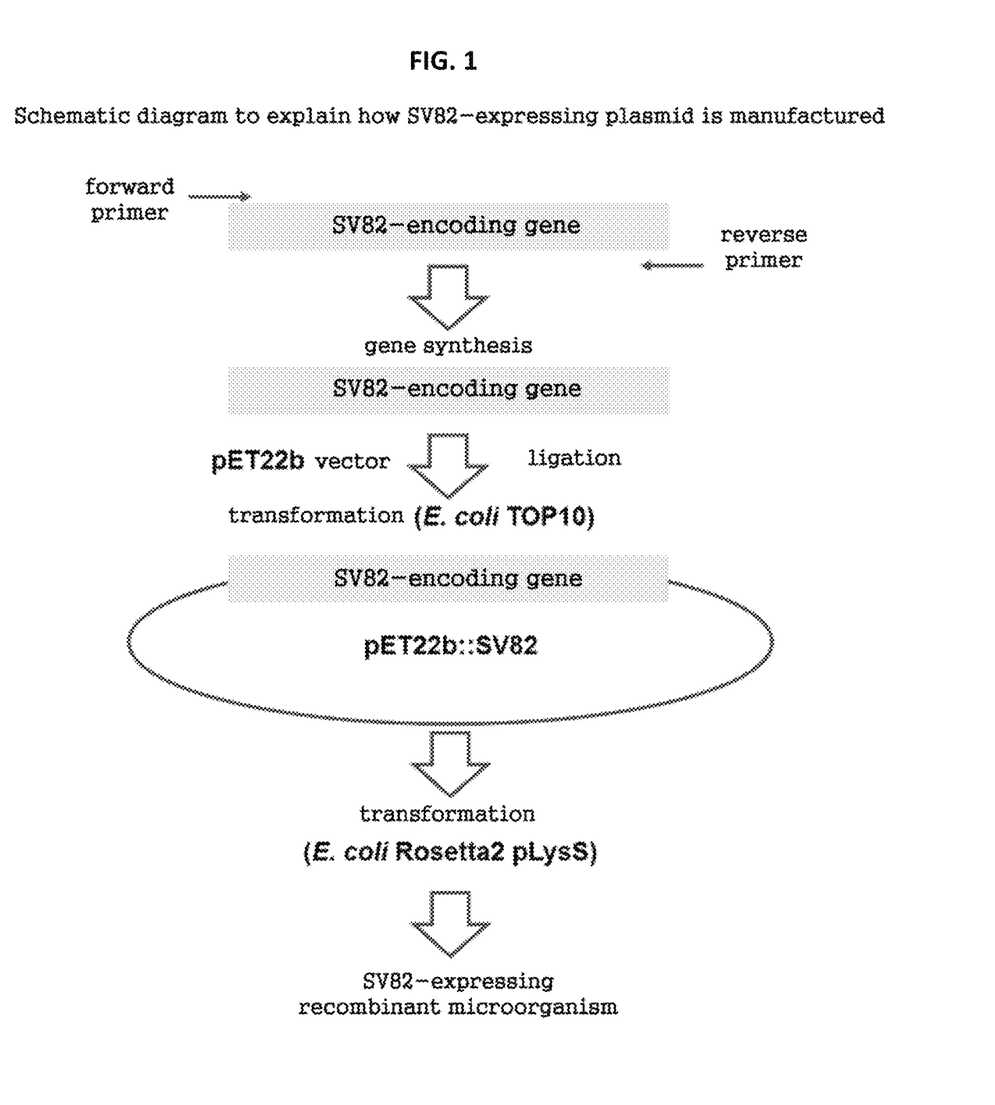
FIG. 1 is a schematic diagram to explain how a recombinant plasmid (pET22b::SV82) comprising a SV82 polypeptide gene is constructed for use in embodiments of the present disclosure and how *Escherichia coli* (*E. coli*) is transformed with the recombinant plasmid (pET22b::SV82)

The gene fragment and a plasmid were cleaved by using an identical restriction enzyme (5' terminus NcoI and 3' terminus XhoI), and the gene fragment was inserted into the plasmid, thereby preparing a recombinant plasmid (pET22b::SV82) (FIG. 1). The recombinant plasmid was used to transform *E. coli* TOP10, and from a host microorganism, gene constructs were obtained in great quantities.

Thereafter, *E. coli* Rosetta2 (DE3) pLysS (Novagen, German) was transformed with the recombinant plasmid to produce a recombinant microorganism for producing SV82 polypeptide.

Example 2. Production of SV82 Polypeptides in Great Quantities and Separation Thereof

*E. coli* Rosetta2 (DE3) pLysS prepared in Example 1 was incubated by using 1 l LB medium (10% tryptophan, 10% sodium chloride and 5% yeast extract), or BSB medium (1% tryptophan, 0.5% yeast extract, 1% glucose and 0.1% HEPES (pH 7.0), Nexgen Biotechnologies. Inc.). In the case of batch incubation, the incubation was performed until $OD_{600}$ reached to be in a range of 0.6 to 0.8. In the case of continuous incubation using a 20 l fermentor, the incubation was performed until $OD_{600}$ reached to be in a range of 20 to 25. Thereafter, 1 to 5 mM IPTG or 2 to 3% lactose was added to these results to induce expression of genes in clones. After the inducing of genes, *E. coli* was incubated 3 to 4 hours more. The cells were collected by centrifuging. These cells were completely suspended in a buffer solution (phosphate buffered saline, 8 g of sodium chloride, 0.2 g of potassium chloride, 1.44 g of sodium phosphate II ($Na_2HPO_4$), 0.24 g of potassium dihydrogen phosphate ($KH_2PO_4$)/l, and pH 7.4), and destroyed by using an ultrasonic crusher. Then, a solution containing intracellular proteins was isolated therefrom.

Figure 2A:
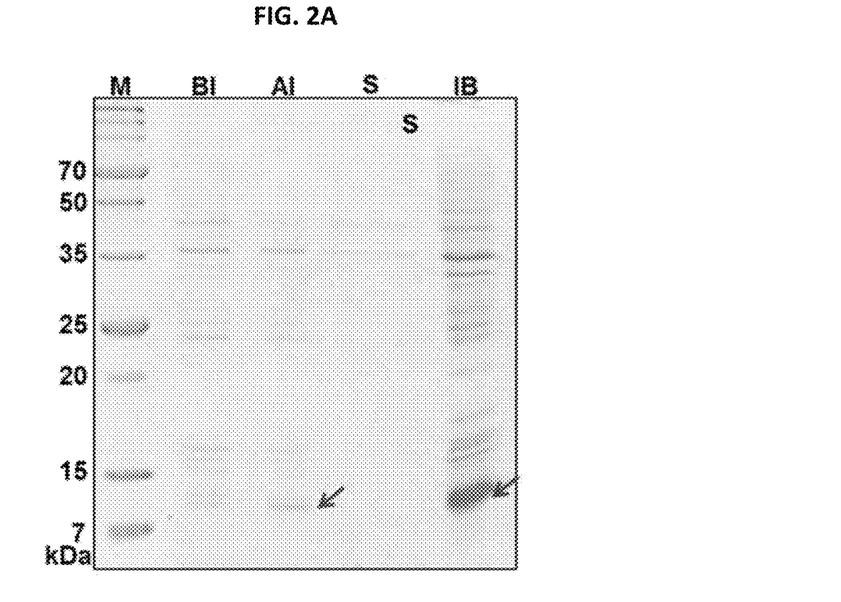
FIGS. 2A and 2B show results of electrophoresis performed on SDS-PAGE gel to identify expression of SV82 polypeptide in *E. coli*. A, 1 l batch incubation, and B, 20 l continuous incubation. M, a size marker; BI, cell crude lysate before expression induction; AI, cell crude lysate after expression induction; S, a total water-soluble protein after expression induction; IB, a total insoluble (inclusion body) protein after expression induction; and an arrow, SV82 polypeptide.
Figure 2B:
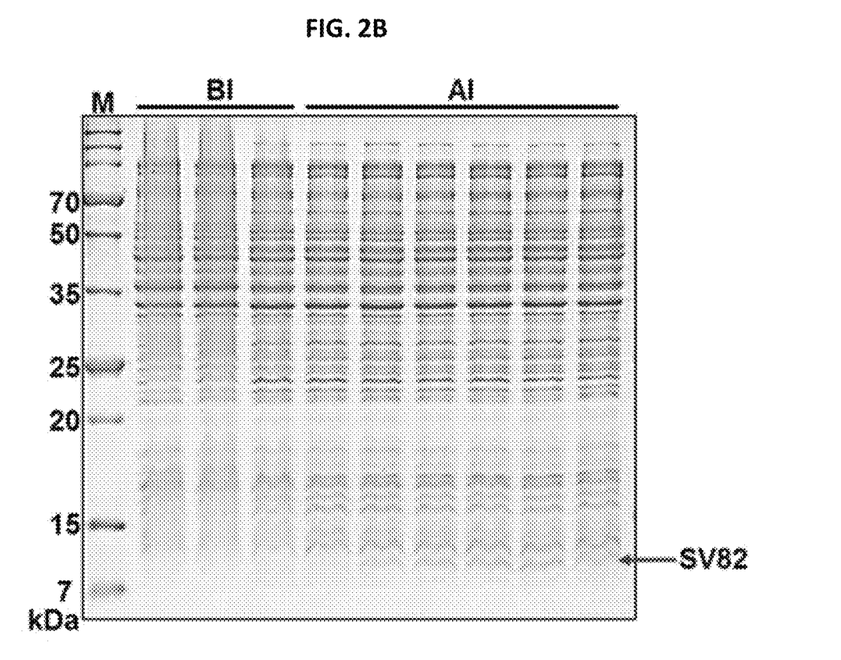

How much SV82 polypeptide was expressed by the expression-induction was identified by 15% SDS-PAGE electrophorosis. As a result, it is seen that 1 l batch incubation (FIG. 2A) or 20 l continuous incubation (FIG. 2B) all has lead a high degree of expression of SV82 polypeptide in the form of inclusion body.

Figure 3:
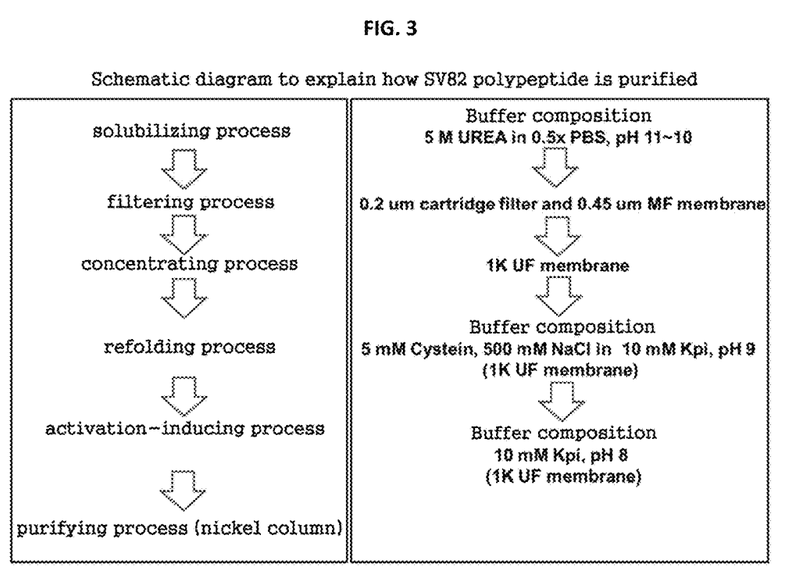
FIG. 3 shows a schematic diagram to explain how to isolate and purify SV82 polypeptide according to an embodiment of the present disclosure.

To purify SV82 polypeptide expressed by the incubation, SV82 polypeptide-containing inclusion bodies were solubilized in a solubilizing buffer solution (5M urea, pH 11), and then, subjected to refolding by using a ultra-fine filtration method (0.45 μm microfiltration membrane and 1 K ultra-fine filtration membrane), and then, to a storage buffer solution (PBS). Thereafter, the separation-purified SV82 polypeptide was passed through a nickel-agarose column at a speed of 3 to 5 ml/min. Subsequently, the column was washed several times by using a buffer solution for binding, and then, 50, 80 and 300 mM imidazole solutions (pH 7.4) were applied to the column to obtain an eluent of SV82 polypeptide through the column in an amount of 20 ml for each application. Then, a 10 mM potassium phosphate buffer was used to remove imidazole therefrom to complete the separation and purification process of SV82 polypeptide. FIG. 3 schematically shows how to purify SV82 polypeptide.

Figure 4A:
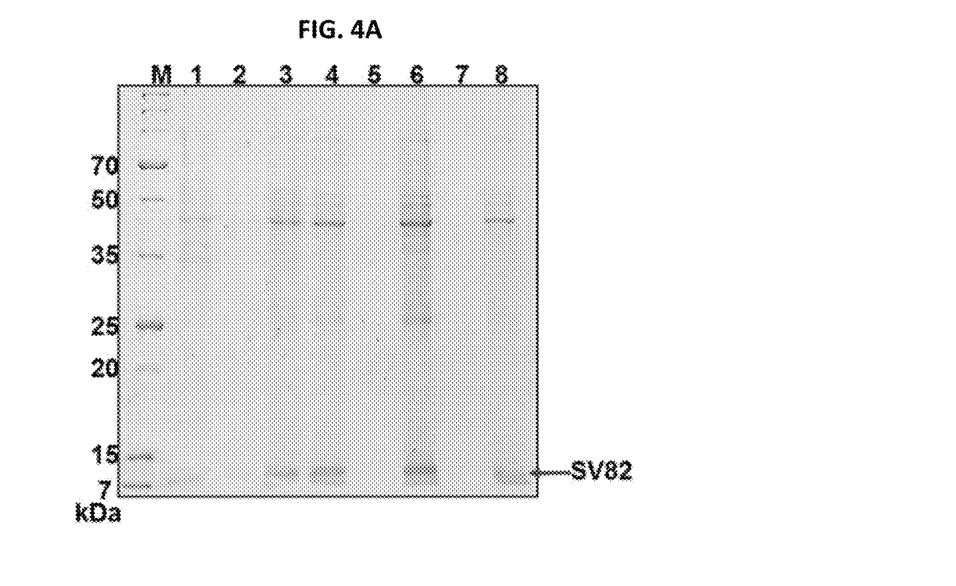
FIGS. 4A and 4B show results of electrophorosis performed on the isolated and purified SV82 polypeptide. A shows an isolation level of SV82 polypeptide during refolding and buffer-exchanging, and B shows electrophoresis results of final SV82 polypeptide isolated by nickel-agarose column. M, a size marker; 1, IB a sample of SV82 polypeptide solubilized; 2, a sample after filtration; 3, a condensed sample; 4, a refolded sample (retentate); 5, a refolded sample (permeate); 6, a buffer exchange sample (retentate); 7, a buffer exchange sample (permeate); 8 and BS, a final sample; UP, a unbound protein; W, a cleaned sample; and E, a column elusion sample.
Figure 4B:
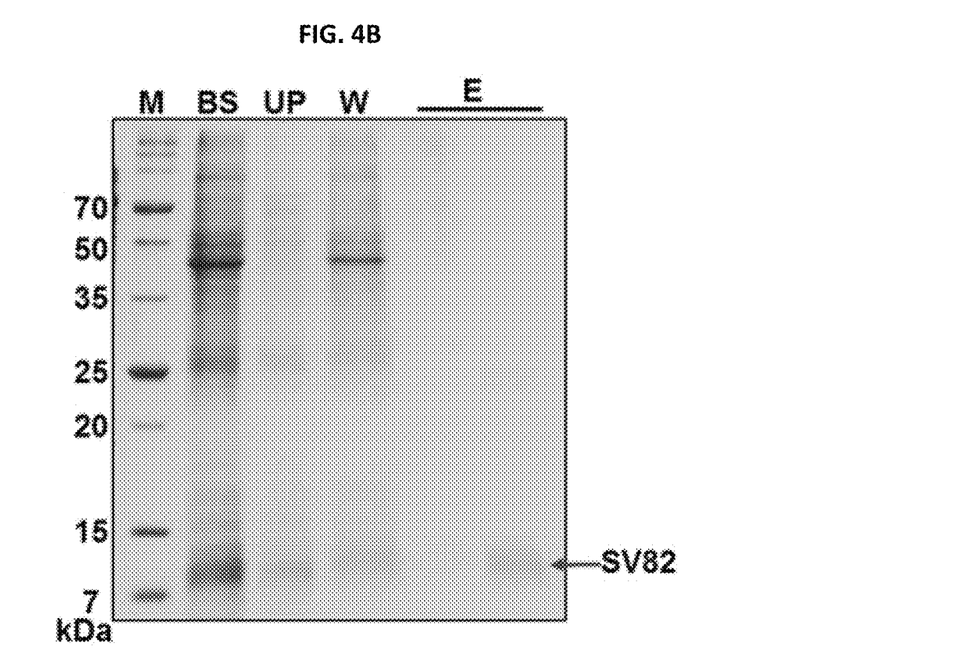

During the separation process of SV82 polypeptide, 15% SDS-PAGE electrophoresis was performed to identify a separation level of protein. As a result, it was confirmed that SV82 polypeptide (SEQ ID NO: 2) was purified by nickel-agarose column (FIGS. 4A and 4B).

Example 3. Measuring Activity of SV82 Polypeptide

Human dermal fibroblast adult (HDFa) cells, which had been cultured to evaluate the activity of SV82 polypeptide that has been separated and purified in Example 2, were treated with SV82 polypeptide having a concentration of 0, 0.02 ppm or 0.2 ppm, and then incubated for 3 days at a temperature of 37° C. Thereafter, the cells were stained by crystal violate staining to identify whether the cells had proliferated.

Figure 5:
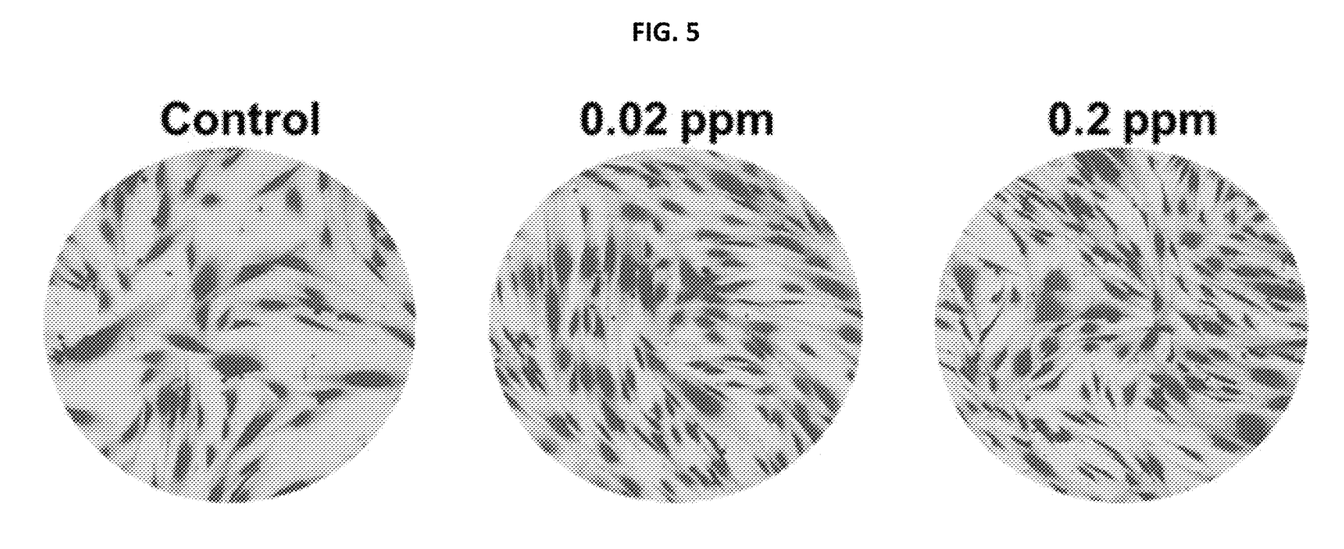
FIG. 5 shows crystal violet staining results to confirm cell proliferation effects of SV82 polypeptide with respect to human dermal fibroblast adult (HDFa).

As a result, referring to FIG. 5, it is seen that compared to a control, the higher concentration (0.02 to 0.2 ppm) SV82 polypeptide has, the more HDFa cells proliferate.

Experimental Example 1. Skin Stimulation Sensory Test on Reduction in Skin Wrinkles and Maintenance in Skin Elasticity Cosmetic compositions were prepared by using the separated and purified SV82 polypeptide as an active ingredient, according to Preparation Examples 1, 2, 3 and 4 and Comparative Examples 1, 2, 3 and 4.

A total of 30 men and women aged 30 or more to less than 60 (10 in their 30s, 10 in their 40s, and 10 in their 50s to 60s) participated in this experiment to evaluate effects associated with skin wrinkles and skin elasticity. For Comparative Example (control), the compositions were applied around their left eyes or left lips where many wrinkles exist once a day for consecutive two weeks; and for Preparation Example (test group), the compositions were applied around their right eyes or right lips where many wrinkles exist once a day for consecutive two weeks. The evaluation results were based on how much wrinkles were reduced around eyes or lips. Regarding the effects for maintaining skin elasticity, the same experiments were performed to count the number of days in which skin elasticity was maintained. Regarding skin stimulation, a sensory test was performed to evaluate skin itching, skin irritation, and skin redness by performing the same experiments. Evaluation results were scaled based on a five-point rule: very good (Point 5), good (Point 4), average (Point 3), bad (Point 2), and very bad (Point 1).

Preparation Example 1 and Comparative Example 1

In Preparation Example 1, a skin lotion was prepared by using SV82 polypeptide as an active ingredient and such components in amounts as shown in Table 1. In Comparative Example 1, a skin lotion was prepared by using such components in amounts as shown in Table 1 without SV82 polypeptide as an active ingredient.

TABLE 1

| | Skin Lotion Composition | |
|---|---|---|
| Components | Preparation Example 1 (wt %) | Comparative Example1 (wt %) |
| SV82 polypeptide | 0.00002 | — |
| amino acids stock | 0.1 | 0.1 |
| Mineral mixture | 0.0007 | 0.0007 |
| Purified water | the balance | the balance |

Skin stimulation sensory tests were performed to identify effects of reducing skin wrinkles and maintaining skin elasticity of the compositions of Preparation Example 1 and Comparative Example 1. The test results are shown in Table 2.

TABLE 2

Sensory test results of Preparation Example 1

| | No. | reducing skin wrinkles – Preparation Example | reducing skin wrinkles – Comparative Example | maintaining skin elasticity – Preparation Example | maintaining skin elasticity – Comparative Example | skin stimulation – Preparation Example |
|---|---|---|---|---|---|---|
| In 30s | 1 | 5 | 4 | 4 | 3 | 4 |
| | 2 | 4 | 3 | 4 | 3 | 4 |
| | 3 | 4 | 5 | 4 | 3.5 | 4 |
| | 4 | 5 | 5 | 4 | 3.5 | 4 |
| | 5 | 5 | 3 | 4 | 3 | 3 |
| | 6 | 4 | 4 | 4 | 3 | 4 |
| | 7 | 5 | 3 | 5 | 3 | 4 |
| | 8 | 5 | 4 | 5 | 3.5 | 4 |
| | 9 | 4 | 3 | 4 | 3 | 3 |
| | 10 | 4 | 3 | 4 | 3 | 3 |
| In 40s | 11 | 5 | 3 | 5 | 4 | 4 |
| | 12 | 4 | 2 | 4 | 2.5 | 4 |
| | 13 | 4 | 2 | 4 | 3 | 4 |
| | 14 | 4 | 3 | 4 | 2.5 | 4 |
| | 15 | 5 | 4 | 5 | 3 | 4.5 |
| | 16 | 5 | 3 | 5 | 3 | 4.5 |
| | 17 | 4 | 3 | 4 | 2.5 | 4 |
| | 18 | 5 | 3.5 | 5 | 3 | 4 |
| | 19 | 4 | 3.5 | 4 | 3 | 4 |
| | 20 | 4 | 3 | 4 | 3 | 5 |
| In 50s to 60s | 21 | 4 | 3.5 | 4 | 3.5 | 4 |
| | 22 | 5 | 3 | 4.5 | 3 | 5 |
| | 23 | 4 | 3 | 4 | 3.5 | 4 |
| | 24 | 4.5 | 3.5 | 4.5 | 3 | 4 |
| | 25 | 4 | 3 | 4 | 2.5 | 4.5 |
| | 26 | 4 | 3 | 4 | 3 | 5 |
| | 27 | 5 | 3 | 4.5 | 3 | 4.5 |
| | 28 | 4 | 3 | 4 | 3 | 5 |
| | 29 | 3.5 | 3.5 | 4 | 3.5 | 4 |
| | 30 | 4 | 3 | 4 | 3 | 4 |
| | Average | 4.4 | 3.3 | 4.3 | 3.1 | 4.1 |

TABLE 4

Sensory test results of Preparation Example 2

| | No. | reducing skin wrinkles – Preparation Example | reducing skin wrinkles – Comparative Example | maintaining skin elasticity – Preparation Example | maintaining skin elasticity – Comparative Example | skin stimulation – Preparation Example |
|---|---|---|---|---|---|---|
| In 30s | 1 | 5 | 4 | 5 | 3 | 4 |
| | 2 | 4 | 3 | 4 | 3 | 4 |
| | 3 | 4 | 3.5 | 4 | 3 | 4.5 |
| | 4 | 4 | 3 | 4 | 3 | 4 |
| | 5 | 5 | 3 | 3 | 3 | 4 |
| | 6 | 4 | 3 | 4 | 3 | 4 |
| | 7 | 4 | 3 | 4 | 3 | 4.5 |
| | 8 | 4 | 3 | 5 | 3 | 4 |
| | 9 | 4 | 3 | 5 | 2 | 4 |
| | 10 | 4 | 2.5 | 4 | 3 | 4 |
| In 40s | 11 | 4 | 3.5 | 5 | 2 | 3.5 |
| | 12 | 4 | 3 | 4 | 2 | 3 |
| | 13 | 4 | 3.5 | 5 | 2 | 4 |
| | 14 | 5 | 3 | 5 | 2 | 4 |
| | 15 | 5 | 3 | 5 | 2 | 4 |
| | 16 | 5 | 3.5 | 4 | 2 | 4 |
| | 17 | 5 | 3.5 | 5 | 2 | 4 |
| | 18 | 5 | 4 | 5 | 3 | 4.5 |
| | 19 | 5 | 3 | 4 | 2 | 4 |
| | 20 | 4 | 2.5 | 5 | 2 | 3 |
| In 50s to 60s | 21 | 5 | 4 | 4 | 2 | 4 |
| | 22 | 5 | 3 | 5 | 2 | 4 |
| | 23 | 5 | 3 | 5 | 2 | 4 |
| | 24 | 5 | 3 | 5 | 2 | 4 |
| | 25 | 4 | 3.5 | 4 | 3 | 4 |
| | 26 | 4 | 3 | 5 | 2 | 4 |
| | 27 | 5 | 3 | 5 | 3 | 4.5 |
| | 28 | 5 | 3.5 | 4 | 2 | 4 |
| | 29 | 4 | 3 | 5 | 3 | 4 |
| | 30 | 5 | 4 | 5 | 2 | 4 |
| | Average | 4.5 | 3.2 | 4.5 | 2.4 | 4.0 |

Preparation Example 2 and Comparative Example 2

In Preparation Example 2, an essence was prepared by using SV82 polypeptide as an active ingredient and such components in amounts as shown in Table 3. In Comparative Example 2, an essence was prepared by using such components in amounts as shown in Table 3 without SV82 polypeptide as an active ingredient.

TABLE 3

Essence composition

| Component | Preparation Example 2 (wt %) | Comparative Example 2 (wt %) |
|---|---|---|
| SV82 polypeptide | 0.00002 | — |
| Amino acids stock | 0.05 | 0.05 |
| Mineral mixture | 0.0007 | 0.0007 |
| Glycerol | 5 | 5 |
| 1,3-butyleneglycol | 10 | 10 |
| Carbopol 940 | 0.3 | 0.3 |
| Purified water | The balance | The balance |

Skin stimulation sensory tests were performed to identify effects of reducing skin wrinkles and maintaining skin elasticity of the compositions of Preparation Example 2 and Comparative Example 2. The test results are shown in Table 4.

Preparation Example 3 and Comparative Example 3

In Preparation Example 3, a lotion was prepared by using SV82 polypeptide as an active ingredient and such components in amounts as shown in Table 5. In Comparative Example 3, a lotion was prepared by using such components in amounts as shown in Table 5 without SV82 polypeptide as an active ingredient.

TABLE 5

Lotion composition

| Component | Preparation Example 3 (wt %) | Comparative Example3 (wt %) |
|---|---|---|
| SV82 polypeptide | 0.00002 | — |
| Amino acids stock | 0.05 | 0.05 |
| Mineral mixture | 0.0007 | 0.0007 |
| Glycerol | 3 | 3 |
| 1,3-butyleneglycol | 10 | 10 |
| Mineral oil | 5 | 5 |
| Cetyl alcohol | 2 | 2 |
| Xanthan Gum | 0.5 | 0.5 |
| Purified water | The balance | The balance |

Skin stimulation sensory tests were performed to identify effects of reducing skin wrinkles and maintaining skin elasticity of the compositions of Preparation Example 3 and Comparative Example 3. The test results are shown in Table 6.

TABLE 6

Sensory test results of Preparation Example 3

| | | reducing skin wrinkles | | maintaining skin elasticity | | skin stimulation |
|---|---|---|---|---|---|---|
| | No. | Preparation Example | Comparative Example | Preparation Example | Comparative Example | Preparation Example |
| In 30s | 1 | 5 | 4 | 5 | 3 | 5 |
| | 2 | 5 | 4 | 5 | 3 | 5 |
| | 3 | 4 | 4 | 4 | 3 | 4 |
| | 4 | 4.5 | 4 | 4.5 | 3 | 5 |
| | 5 | 4 | 4 | 4 | 3 | 4 |
| | 6 | 3.5 | 4 | 3.5 | 2.5 | 4 |
| | 7 | 4 | 3.5 | 4 | 3 | 4 |
| | 8 | 4.5 | 3 | 4.5 | 3 | 5 |
| | 9 | 4.5 | 3.5 | 4.5 | 3 | 5 |
| | 10 | 4 | 3.5 | 4 | 3 | 4 |
| In 40s | 11 | 3.5 | 3.5 | 3.5 | 2 | 3 |
| | 12 | 3 | 2.5 | 3 | 2.5 | 3 |
| | 13 | 3 | 3.5 | 3 | 3 | 3 |
| | 14 | 4.5 | 4 | 4.5 | 3 | 5 |
| | 15 | 4.5 | 4 | 4.5 | 4 | 5 |
| | 16 | 5 | 3.5 | 5 | 4 | 4.5 |
| | 17 | 4 | 3 | 4 | 3 | 4.5 |
| | 18 | 5 | 3.5 | 5 | 3 | 5 |
| | 19 | 5 | 3.5 | 5 | 3 | 4.5 |
| | 20 | 5 | 3 | 5 | 3 | 5 |
| In 50s to 60s | 21 | 5 | 3.5 | 5 | 3.5 | 5 |
| | 22 | 5 | 3.5 | 5 | 3.5 | 4.5 |
| | 23 | 5 | 3.5 | 5 | 3.5 | 4 |
| | 24 | 5 | 3 | 5 | 3 | 5 |
| | 25 | 4 | 3.5 | 4 | 3.5 | 5 |
| | 26 | 4 | 3.5 | 4 | 3.5 | 4 |
| | 27 | 4.5 | 3 | 4.5 | 3 | 4 |
| | 28 | 4.5 | 3 | 4.5 | 3 | 4 |
| | 29 | 4 | 3 | 4 | 3.5 | 4.5 |
| | 30 | 4 | 3 | 4 | 3 | 4 |
| | Average | 4.4 | 3.5 | 4.4 | 3.1 | 4.4 |

Preparation Example 4 and Comparative Example 4

In Preparation Example 4, a cream was prepared by using SV82 polypeptide as an active ingredient and such components in amounts as shown in Table 5. In Comparative Example 4, a cream was prepared by using such components in amounts as shown in Table 7 without SV82 polypeptide as an active ingredient.

TABLE 7

Cream composition

| Component | Preparation Example 4 (wt %) | Comparative Example 4 (wt %) |
|---|---|---|
| SV82 polypeptide | 0.00002 | — |
| Amino acids stock | 0.05 | 0.05 |
| Mineral mixture | 0.0007 | 0.0007 |
| Glycerol | 2 | 2 |
| Mineral oil | 10 | 10 |
| Sorbitan olivate | 3 | 3 |
| Cetyl alcohol | 2 | 2 |
| Purified water | The balance | The balance |

Skin stimulation sensory tests were performed to identify effects of reducing skin wrinkles and maintaining skin elasticity of the compositions of Preparation Example 4 and Comparative Example 4. The test results are shown in Table 8.

TABLE 8

Sensory test results of Preparation Example 4

| | | reducing skin wrinkles | | maintaining skin elasticity | | skin stimulation |
|---|---|---|---|---|---|---|
| | No. | Preparation Example | Comparative Example | Preparation Example | Comparative Example | Preparation Example |
| In 30s | 1 | 4.5 | 4 | 4.5 | 3 | 5 |
| | 2 | 5 | 4.5 | 5 | 4 | 5 |
| | 3 | 4.5 | 4 | 4 | 3 | 5 |
| | 4 | 4.5 | 4 | 4 | 3.5 | 4 |
| | 5 | 4 | 4 | 4 | 3 | 4 |
| | 6 | 4 | 3.5 | 4 | 3.5 | 4 |
| | 7 | 2.5 | 3.5 | 4.5 | 3.5 | 3 |
| | 8 | 2.5 | 3.5 | 4 | 3.5 | 3 |
| | 9 | 3.5 | 3 | 4 | 3 | 3 |
| | 10 | 3.5 | 3 | 4 | 3 | 4 |
| In 40s | 11 | 4 | 3 | 4 | 3.5 | 4 |
| | 12 | 3 | 2 | 3 | 2 | 3 |
| | 13 | 3.5 | 3 | 4 | 2 | 3 |
| | 14 | 3.5 | 4 | 4 | 3 | 4 |
| | 15 | 4 | 3.5 | 4 | 3.5 | 4 |
| | 16 | 4.5 | 3 | 5 | 3 | 4.5 |
| | 17 | 4 | 3.5 | 5 | 3.5 | 4.5 |
| | 18 | 4.5 | 3.5 | 4.5 | 3 | 4 |
| | 19 | 4.5 | 4 | 5 | 4 | 4.5 |
| | 20 | 5 | 3 | 5 | 3 | 4.5 |
| In 50s to 60s | 21 | 4.5 | 3 | 5 | 3 | 5 |
| | 22 | 5 | 3.5 | 5 | 3.5 | 5 |
| | 23 | 4.5 | 3.5 | 4.5 | 3.5 | 5 |
| | 24 | 4 | 3 | 4 | 3.5 | 4.5 |
| | 25 | 5 | 3 | 5 | 3.5 | 5 |
| | 26 | 5 | 3 | 5 | 3.5 | 4.5 |
| | 27 | 5 | 3.5 | 5 | 3.5 | 4.5 |
| | 28 | 4.5 | 3 | 5 | 3 | 5 |
| | 29 | 4.5 | 4 | 4.5 | 3.5 | 5 |
| | 30 | 4.5 | 4 | 4.5 | 3 | 5 |
| | Average | 4.2 | 3.4 | 4.4 | 3.2 | 4.3 |

The sensory test results show that Preparation Examples 1, 2, 3, and 4 comprising SV82 polypeptide as an active ingredient had better effects for reducing skin wrinkles and maintaining skin elasticity than Comparative Examples 1, 2, 3, and 4.

A method of producing SV82 polypeptide by using a SV82 polypeptide-encoding gene that is optimized for the codon of *E. coli*, according to embodiments of the present disclosure, enables SV82 polypeptide to be produced in great quantities, and a cosmetic composition for reducing skin wrinkles and maintaining skin elasticity comprising the SV82 polypeptide as an active ingredient, according to embodiments of the present disclosure, may induce intradermal peripheral nerve stimulation when applied in a small amount on the skin, leading to reducing skin wrinkles and maintaining skin elasticity. Accordingly, the cosmetic composition can be used in functional cosmetic products or aesthetic plastic surgery.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A spider venom (SV) 82 polypeptide having the amino acid sequence of SEQ ID NO: 2.

2. A spider venom (SV) polypeptide-encoding gene having the nucleotide sequence of SEQ ID NO: 1, which is optimized for a codon of *Escherichia coli* (*E. coli*).

3. A recombinant vector comprising the SV polypeptide-encoding gene of claim 2.

4. An *E. coli* transformed with the recombinant vector of claim 3.

5. A cosmetic composition for reducing skin wrinkles and maintaining skin elasticity, the cosmetic composition comprising, as an active ingredient, a spider venom (SV) 82 polypeptide having the amino acid sequence of SEQ ID NO: 2.

6. The cosmetic composition of claim 5, wherein an amount of the SV82 polypeptide is in a range of 0.000001 to 0.0001 wt % based on a total weight of the cosmetic composition.

7. The cosmetic composition of claim 5, wherein the cosmetic composition has any one formulation selected from skin lotion, skin softener, skin toner, astringent, lotion, milk lotion, moisture lotion, nutrition lotion, massage cream, nutrition cream, eye cream, moisture cream, hand cream, essence, nutrition essence, cleansing foam, cleansing water, cleansing lotion, cleansing cream, body lotion, body cleanser, a soap, and powder.

8. The cosmetic composition of claim 5, further comprising one or more adjuvants selected from a fatty substance, an organic solvent, a solubilizer, a thickening agent, a gelling agent, a softener, an antioxidant, a suspending agent, a stabilizer, a foaming agent, an odorant, a surfactant, water, an ionic or non-ionic emulsifying agent, a filler, an agent for blocking metallic ions, a chelating agent, a preserving agent, a vitamin, a moisturizing agent, essential oil, a dye, a pigment, a hydrophilic or hydrophobic activator, and a lipid vesicle.

9. The spider venom (SV) 82 polypeptide of claim 1, consisting of the amino acid sequence of SEQ ID NO: 2.

10. The spider venom (SV) polypeptide-encoding gene of claim 2, consisting of the nucleotide sequence of SEQ ID NO: 1.

11. The cosmetic composition of claim 5, wherein the spider venom (SV) 82 polypeptide consists of the amino acid sequence of SEQ ID NO: 2.

12. A method of producing spider venom (SV) 82 polypeptide in a host cell, the method comprising transforming the host cell with the recombinant vector of claim 3 to overexpress a SV82 polypeptide-encoding gene.

13. The method of claim 12, wherein the host cell is *Escherichia coli* (*E. coli*).

* * * * *